US008075153B2

(12) United States Patent
Werner

(10) Patent No.: US 8,075,153 B2
(45) Date of Patent: Dec. 13, 2011

(54) COMBINATION HEARING PROTECTOR AND ILLUMINATION PROVIDER

(76) Inventor: Theodore J. Werner, Huntington Station, NY (US)

( * ) Notice: Subject to any disclaimer, the term of this patent is extended or adjusted under 35 U.S.C. 154(b) by 1315 days.

(21) Appl. No.: 11/542,998

(22) Filed: Oct. 4, 2006

(65) Prior Publication Data

US 2007/0154029 A1 Jul. 5, 2007

Related U.S. Application Data

(60) Provisional application No. 60/756,003, filed on Jan. 4, 2006.

(51) Int. Cl.
*F21V 21/084* (2006.01)

(52) U.S. Cl. ............ 362/105; 362/103; 362/800; 2/423; 2/209; 128/866

(58) Field of Classification Search .......... 362/103–105; 2/423, 208, 209; 128/864, 866
See application file for complete search history.

(56) References Cited

U.S. PATENT DOCUMENTS

| | | | | |
|---|---|---|---|---|
| 4,969,069 A | * | 11/1990 | Eichost | 362/105 |
| 5,894,113 A | * | 4/1999 | Wingate | 181/141 |
| 5,951,141 A | * | 9/1999 | Bradley | 362/105 |
| 6,095,146 A | * | 8/2000 | Knauer et al. | 128/864 |
| 6,834,978 B2 | * | 12/2004 | Mehler et al. | 362/190 |
| 6,918,678 B2 | * | 7/2005 | McClanahan | 362/105 |
| 7,020,902 B1 | * | 4/2006 | Tyler | 2/209 |
| 7,114,823 B2 | * | 10/2006 | McCullough et al. | 362/105 |
| 2005/0207143 A1 | * | 9/2005 | Bishop et al. | 362/106 |

* cited by examiner

*Primary Examiner* — Robert May
*Assistant Examiner* — Leah S Lovell
(74) *Attorney, Agent, or Firm* — Charles E. Baxley

(57) ABSTRACT

A combination hearing protector and illumination provider, including a right cup, a left cup, a band, a first light source, and a second light source. The right cup covers the right ear of a user. The left cup covers the left ear of the user. The band connects the right cup to the left cup and is worn over the top of the head of the user. The first light source is operatively connected to one of the right cup and the left cup and faces in a direction that is one of forward of the user and rearward of the user. The second light source is operatively connected to one of the right cup and the left cup and faces in a direction that is the other of forward of the user and rearward of the user. The first light source and the second light source illuminate in opposite directions to each other so as to illuminate forward of the user and rearward of the user.

29 Claims, 5 Drawing Sheets

COMBINATION HEARING PROTECTOR AND ILLUMINATION PROVIDER

1. CROSS REFERENCE TO RELATED APPLICATIONS

The instant non-provisional patent application claims priority from provisional patent application No. 60/756,003, filed on Jan. 4, 2006, and entitled HEARING PROTECTORS WITH LIGHTING SYSTEMS.

2. BACKGROUND OF THE INVENTION

A. Field of the Invention

The embodiments of the present invention relate to a hearing protector, and more particularly, the embodiments of the present invention relate to a combination hearing protector and illumination provider.

B. Description of the Prior Art

Environmental sounds typically include a mixture of various sound wave frequencies having varying intensities.

It is well documented that repeated or prolonged exposure to sounds of a sufficiently high sound pressure level will cause temporary or permanent hearing loss. For example, exposure to sound waves of some frequencies and of varying intensities under conditions of severe impact can damage the auditory organ and cause serious hearing problems including deafness.

Injurious noises, such as those caused by explosions or bursts, often include a mixture of sound frequencies of varying intensity. These disturbing frequencies are in both the high and low frequency bands and have an intensity sufficient to cause hearing problems. Individuals who are frequently exposed to sounds having such disturbing—and sometimes dangerous—frequencies and intensities run the risk of incurring injuries, such as hearing loss or even deafness. These individuals include workers at demolition or construction sites, operators of heavy, noisy equipment, and those in active military service.

Ear, i.e. hearing, protection is needed to prevent loss in hearing acuity and the gradual increase in the threshold of hearing resulting from extended exposures to loud noise. Hearing protective devices are designed to reduce negative effects of exposure to dangerous frequencies by limiting the entry of all sound waves into the auditory organ.

Hearing protectors fall generally into three categories including protectors capping the entrance to the ear canal, protectors entering the ear canal and sealing the ear canal prior to the bend in the ear canal—usually referred to simply as semi-insert devices, and protectors entering the ear canal and taking the bend in the ear canal—sometimes referred to as banded earplugs. Semi-insert hearing protectors generally protect similarly to earplugs, but usually to a lesser level, and are also referred to as semi-aural hearing protectors.

Hearing protective devices are worn in a wide variety of environments. In many instances, these hearing protective devices are worn in dark or limited light environments. When the hearing protective devices are worn in a dark environment, there are additional factors that should be considered. For example, because the hearing protective devices are designed to attenuate noise, there is an increased chance that an individual in a given environment may not be aware of events happening around the wearer, especially when it is dark out and the eyesight of the wearer is limited due to this darkness. It is also more difficult to locate objects laid down or accidently dropped in a dark environment.

Hearing protectors frequently are worn by people who are exposed to dangerous conditions. Having the hearing protectors over ones ears may in fact present additional dangers to the wearer. Further, the wearer may need to use the hands while working to illuminate the working space.

Under various circumstances of employment, it is necessary for workers to wear ear muffs to protect their ears from an overly noisy environment or to wear headphones for protection from noise and for communication in spite of the noise. There are occasions when the work being done in these noisy environments is not adequately illuminated, and it would be useful to be able to wear head-mounted lights as well as ear covering apparatus.

Numerous innovations for ear coverings have been provided in the prior art, which will be described below in chronological order to show advancement in the art, and which are incorporated herein by reference thereto. Even though these innovations may be suitable for the specific individual purposes to which they address, they each differ in structure, and/or operation, and/or purpose from the embodiments of the present invention, in that they do not teach a combination hearing protector and illumination provider.

(1) U.S. Pat. No. 4,969,069 to Eichost.

U.S. Pat. No. 4,969,069 issued to Eichost on Nov. 6, 1990 in class 362 and subclass 105 teaches lights incorporated in or attached to ear covering apparatus, such as ear muffs and earphones, and directed to illuminate a work area in front of the wearer of the apparatus. The lights are positioned low on the ear covering apparatus to avoid reflection of light into a wearer's eyes by eyeglasses.

(2) U.S. Pat. No. 5,894,113 to Wingate.

U.S. Pat. No. 5,894,113 issued to Wingate on Apr. 13, 1999 in class 181 and subclass 141 teaches a method and apparatus of providing a personalized light source in conjunction with a sound system, including mounting a personalized light source on a support for supporting at least one speaker next to a wearer's ear. The personalized light source includes an effective light source mounted at the distal end of a semi-flexible stem. The stem allows the effective light source to be aimed as desired by the wearer and may be extended from or retracted into the support.

(3) U.S. Pat. No. 5,951,141 to Bradley.

U.S. Pat. No. 5,951,141 issued to Bradley on Sep. 14, 1999 in class 362 and subclass 105 teaches a head mounted illumination device, including a light source disposed within a housing. The light source includes a plurality of lights disposed within the housing. The housing is securable to a mouthpiece of a headset to facilitate securement of the light source to the headset. An activation button is disposed within the housing. The activation button is in communication with the light source. The activation button includes a contact switch extending outwardly of the housing. The contact switch aligns with a lip of a user. A power source is securable to the headset. The power source includes wiring extending outwardly therefrom. The wiring couples with the activation button to facilitate communication therewith.

(4) U.S. Pat. No. 6,095,146 to Knauer et al.

U.S. Pat. No. 6,095,146 issued to Knauer et al. on Aug. 1, 2000 in class 128 and subclass 864 teaches hearing protective devices having glow-in-the-dark properties. In an exemplary embodiment, the hearing protective device includes a semi-aural device, an earplug, or an earmuff device. In all embodiments, a glow-in-the-dark material is incorporated into at least a part of the earing protective device so that the glow-in-the-dark material continues to emit light for an extended period of time in a dark environment after the material has been excited by irradiation. Preferred and exemplary glow-in-the-dark materials include phosphorescent materials. The glow-in-the-dark materials may be disposed on a surface of the hearing protective part or dispersed throughout the material forming this part.

(5) U.S. Pat. No. 6,834,978 to Mehler et al.

U.S. Pat. No. 6,834,978 issued to Mehler et al. on Dec. 28, 2004 in class 362 and subclass 190 teaches an earpiece light. In particular, an earpiece having a power supply and a light source mounted on the earpiece. The earpiece light is preferably for use on a person's outer ear. The earpiece light includes an ear support, preferably for placement behind the user's crest of helix. The ear support is attached to a power supply housing, preferably for placement over the user's external auditory canal. The power supply housing has a power supply and a lamp arm, with a distal end extended from the power supply housing. The power supply is connected to a light source mounted on the distal end of the lamp arm. Preferably, the lamp arm is positioned below the ear support, and the power supply is connected to a light source, preferably an LED, mounted on the lamp arm.

(6) United States Patent Application Publication No. 2005/0207143 to Bishop et al.

United States Patent Application Publication No. 2005/0207143 published to Bishop et al. on Sep. 22, 2005 in class 362 and subclass 106 teaches a flashing safety headwear, including affixing with glue a light assembly through the underside of a cap. A commercially available battery pack with a switch is placed in a rear battery pouch. The batteries are connected to the lamp by wiring a series electrical circuit. Wires from the batteries serving the light and switch assembly are routed through the inner lining of the cap. The wires are then soldered to the lamp and controlled off and on by the switch. The light is intended to be used anytime visibility is restricted due to no or low light conditions in order to alert any person to the presence of another individual.

(7) U.S. Pat. No. 7,020,902 to Tyler.

U.S. Pat. No. 7,020,902 issued to Tyler on Apr. 4, 2006 in class 2 and subclass 209 teaches a heated ear guard for warming the ears of a user, having a pair of reflector assemblies and a headband extending between the reflector assemblies for positioning the reflector assemblies over the ears of the user. Each reflector assembly has an open end, a light bulb, and orients light from the light bulb toward the open end. When the opened end is positioned over the ears, the light bulbs radiate heat to the ears. The reflector assemblies may include a translucent peripheral ring encircling the open end and allowing some light to escape thereat to enhance the visibility of the user.

It is apparent that numerous innovations for ear coverings have been provided in the prior art that are adapted to be used. Furthermore, even though these innovations may be suitable for the specific individual purposes to which they address, they would not be suitable for the purposes of the embodiments of the present invention as heretofore described, namely, a combination hearing protector and illumination provider.

3. SUMMARY OF THE INVENTION

Thus, an object of the embodiments of the present invention is to provide a combination hearing protector and illumination provider that avoids the disadvantages of the prior art.

Briefly stated, another object of the embodiments of the present invention is to provide a combination hearing protector and illumination provider, including a right cup, a left cup, a band, a first light source, and a second light source. The right cup covers the right ear of a user. The left cup covers the left ear of the user. The band connects the right cup to the left cup and is worn over the top of the head of the user. The first light source is operatively connected to one of the right cup and the left cup and faces in a direction that is one of forward of the user and rearward of the user. The second light source is operatively connected to one of the right cup and the left cup and faces in a direction that is the other of forward of the user and rearward of the user. The first light source and the second light source illuminate in opposite directions to each other so as to illuminate forward of the user and rearward of the user.

The novel features considered characteristic of the embodiments of the present invention are set forth in the appended claims. The embodiments of the present invention themselves, however, both as to their construction and their method of operation, together with additional objects and advantages thereof, will be best understood from the following description of the specific embodiments when read and understood in connection with the accompanying drawing.

4. BRIEF DESCRIPTION OF THE DRAWING

The figures of the drawing are briefly described as follows.

5. LIST OF REFERENCE NUMERALS UTILIZED IN THE DRAWING

Figure 1:
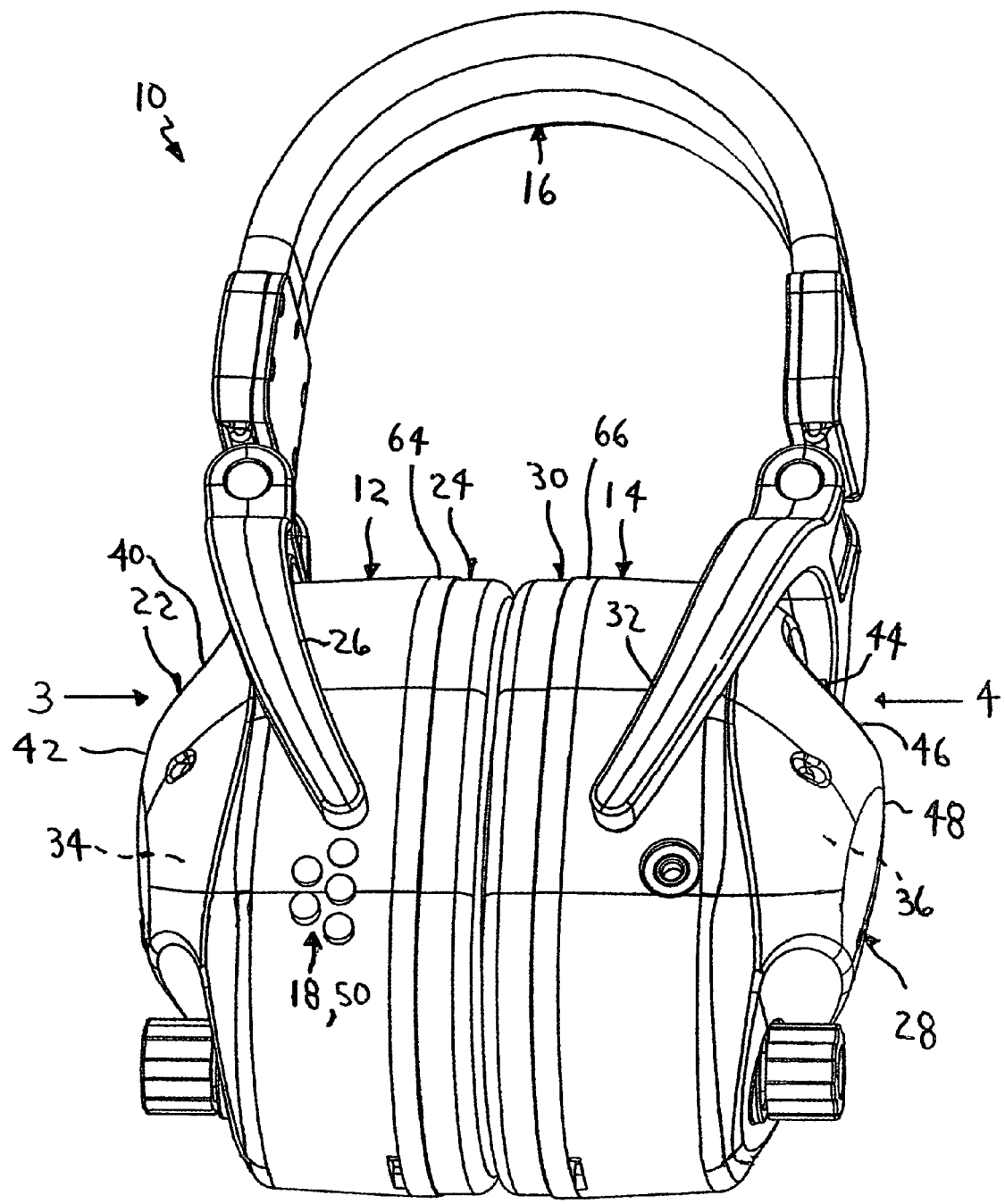
FIG. 1 is a diagrammatic front perspective view of the combination hearing protector and illumination provider of the embodiments of the present invention.
Figure 2:
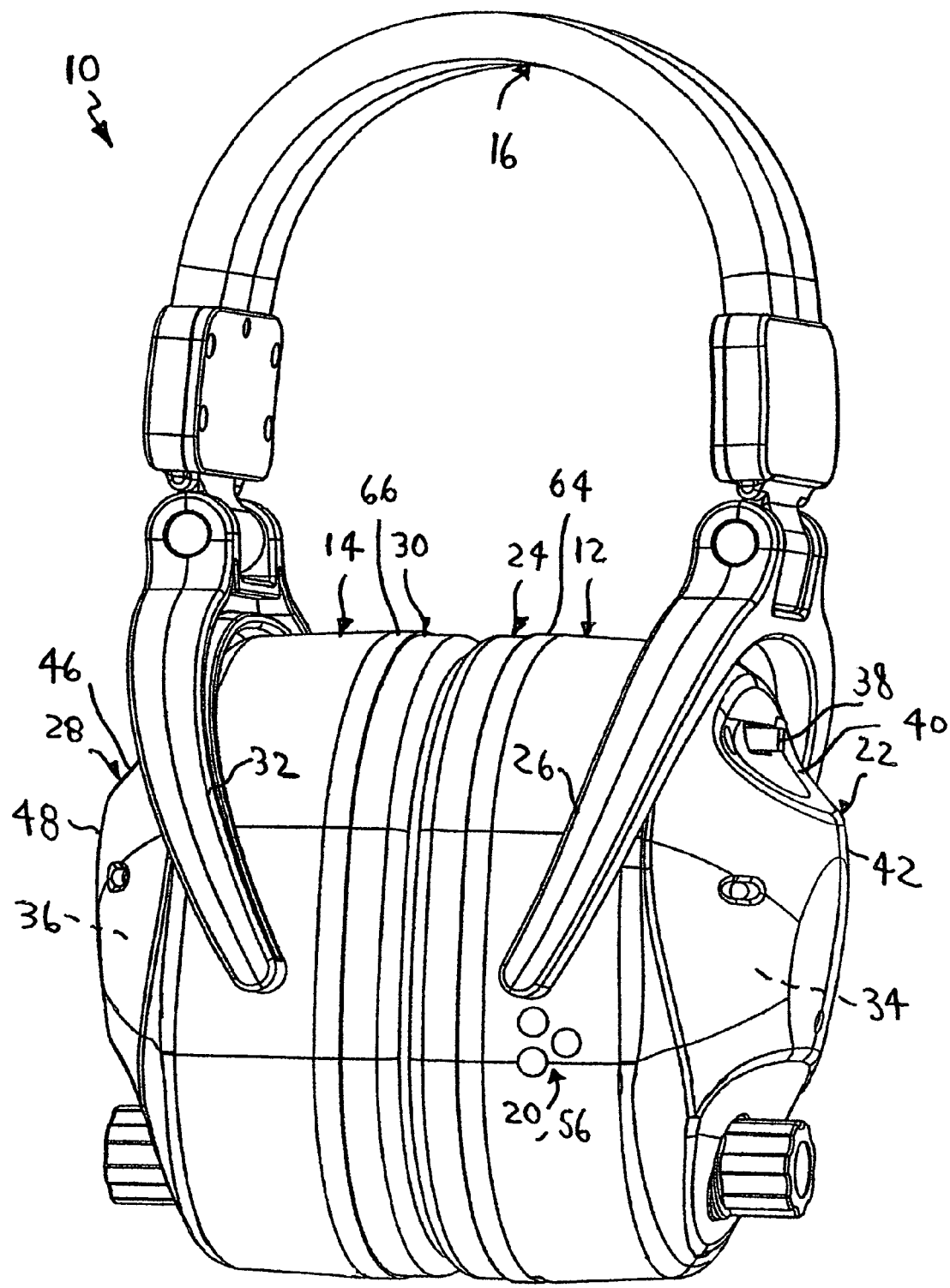
FIG. 2 is a diagrammatic rear perspective view of the combination hearing protector and illumination provider of the embodiments of the present invention.
Figure 3:
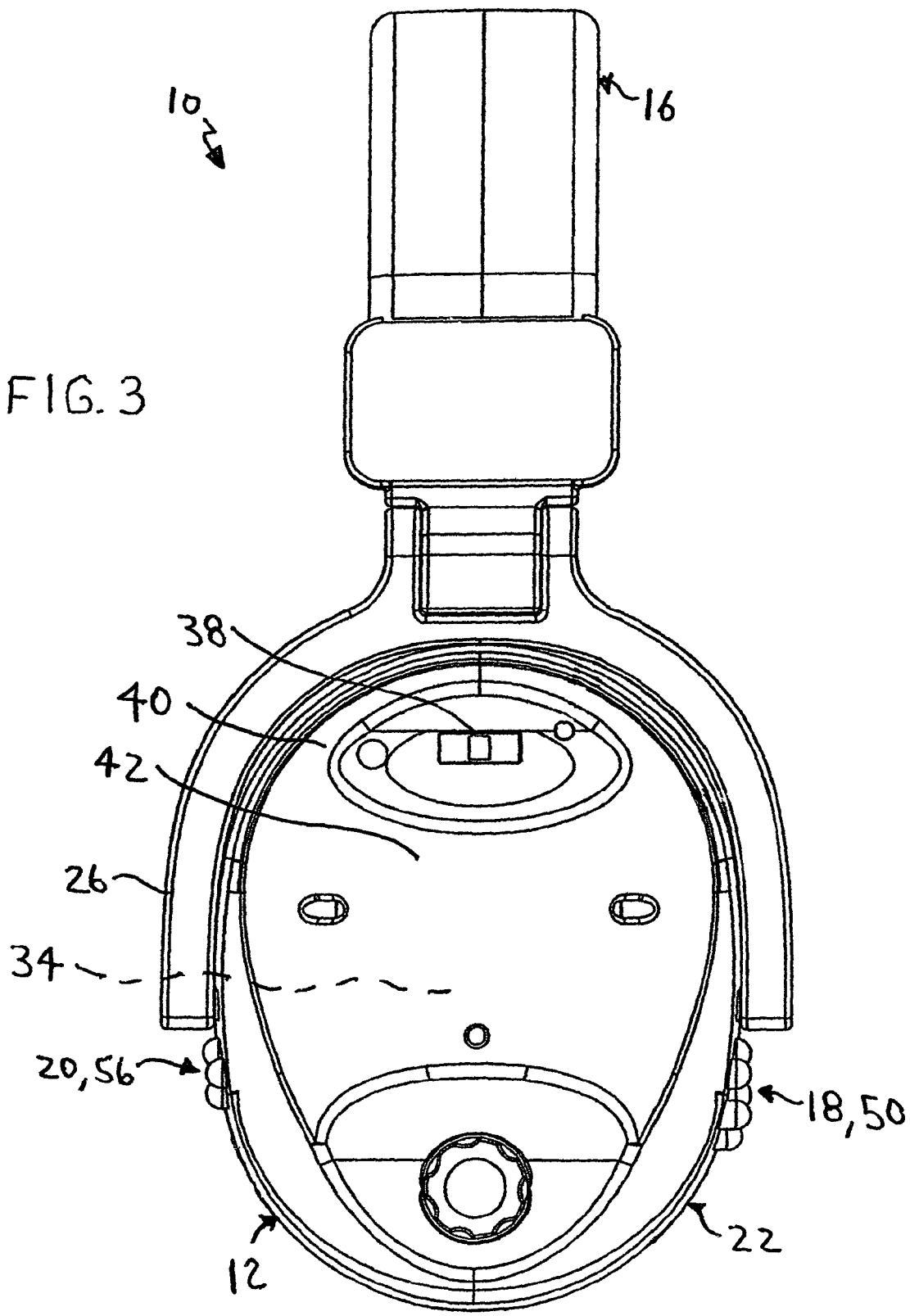
FIG. 3 is a diagrammatic right side elevational view taken generally in the direction of ARROW 3 in FIG. 1 of the combination hearing protector and illumination provider of the embodiments of the present invention.

A. General.

10 combination hearing protector and illumination provider of embodiments of present invention B. Combination Hearing Protector and Illumination Provider 10.

12 right cup for covering right ear of user

14 left cup for covering left ear of user

16 band for wearing over top of head of user

18 first light source for facing in direction being one of forward of user and rearward of user

20 second light source for facing in direction being other of forward of user and rearward of user

22 right casing of right cup 12

24 right pad of right cup 12 for providing comfort for right ear of user

26 one end of band 16

28 left casing of left cup 14

30 left pad of left cup 14 for providing comfort for left ear of user

32 other end of band 16

34 right power supply interface of right cup 12 for electrically communicating with power supply, such as battery, for powering first light source 18

36 left power supply interface of left cup 14 for electrically communicating with power supply, such as battery, for powering second light source 20

38 right activation switch of right cup 12
40 upper portion of outboard side 42 of right casing 22 of right cup 12
42 outboard side of right casing 22 of right cup 12
44 left activation switch of left cup 14
46 upper portion of outboard side 48 of left casing 28 of left cup 14
48 outboard side of left casing 28 of left cup 14
50 plurality of first LEDs 50 of first light source 18
56 plurality of second LEDs of second light source 20
64 right sound barrier of right cup 12
66 left sound barrier of left right cup 14

6. DETAILED DESCRIPTION OF THE PREFERRED EMBODIMENTS

A. General

Referring now to the figures, in which like numerals indicate like parts, and particularly to FIGS. 1-4, which are, respectively, a diagrammatic front perspective view of the combination hearing protector and illumination provider of the embodiments of the present invention, a diagrammatic rear perspective view of the combination hearing protector and illumination provider of the embodiments of the present invention, a diagrammatic right side elevational view taken generally in the direction of ARROW 3 in FIG. 1 of the combination hearing protector and illumination provider of the embodiments of the present invention, and a diagrammatic left side elevational view taken generally in the direction of ARROW 4 in FIG. 1 of the combination hearing protector and illumination provider of the embodiments of the present invention, the combination hearing protector and illumination provider of the embodiments of the present invention is shown generally at 10.

B. The Combination Hearing Protector and Illumination Provider 10

The combination hearing protector and illumination provider 10 comprises a right cup 12 for covering the right ear of a user, a left cup 14 for covering the left ear of the user, and a band 16 connecting the right cup 12 to the left cup 14 and for wearing over the top of the head of the user.

The combination hearing protector and illumination provider 10 further comprises a first light source 18 and a second light source 20. The first light source 18 is operatively connected to one of the right cup 12 and the left cup 14 and is for facing in a direction that is one of forward of the user and rearward of the user. The second light source 20 is operatively connected to one of the right cup 12 and the left cup 14 and is for facing in a direction that is the other of forward of the user and rearward of the user. The first light source 18 and the second light source 20 illuminate in opposite directions to each other for illuminating forward of the user and rearward of the user.

The right cup 12 comprises a right casing 22 and a right pad 24. The right casing 22 of the right cup 12 is operatively connected to one end 26 of the band 16. The right pad 24 of the right cup 12 is for providing comfort for the right ear of the user, and is detachably mounted to the right casing 22 of the right cup 12 so as to allow replacement of the right pad 24 of the right cup 12 and servicing access into the right casing 22 of the right cup 12 when necessary.

The left cup 14 comprises a left casing 28 and a left pad 30. The left casing 28 of the left cup 14 is operatively connected to the other end 32 of the band 16. The left pad 30 of the left cup 14 is for providing comfort for the left ear of the user, and is detachably mounted to the left casing 28 of the left cup 14 so as to allow replacement of the left pad 30 of the left cup 14 and servicing access into the left casing 28 of the left cup 14 when necessary.

The band 16 is made from a material selected from the group consisting of metal, plastic, and combinations thereof.

The right cup 12 further comprises a right power supply interface 34. The right power supply interface 34 of the right cup 12 is disposed in the right casing 22 of the right cup 12, is in electrical communication with the first light source 18, and is for electrically communicating with a power supply, such as a battery, for powering the first light source 18.

The left cup 14 further comprises a left power supply interface 36. The left power supply interface 36 of the left cup 14 is disposed in the left casing 28 of the left cup 14, is in electrical communication with the second light source 20, and is for electrically communicating with a power supply, such as a battery, for powering the second light source 20.

The right power supply interface 34 of the right cup 12 and the left power supply interface 36 of the left cup 14 are independent of each other so if the power supply of one of the first light source 18 and the second light source 20 fails, the other of the one of the first light source 18 and the second light source 20 will not fail.

The right cup 12 further comprises a right activation switch 38. The right activation switch 38 of the right cup 12 is preferably a slide switch, is in series electrical communication with both the first light source 18 and the right power supply interface 34 of the right cup 12 to selectively power the first light source 18, is disposed in the right casing 22 of the right cup 12, and is accessible from an upper portion 40 of an outboard side 42 of the right casing 22 of the right cup 12.

The left cup 14 further comprises a left activation switch 44. The left activation switch 44 of the left cup 14 is preferably a slide switch, is in series electrical communication with both the second light source 20 and the left power supply interface 36 of the left cup 14 to selectively power the second light source 20, is disposed in the left casing 28 of the left cup 14, and is accessible from an upper portion 46 of an outboard side 48 of the left casing 28 of the left cup 14.

The first light source 18 is preferably a plurality of first LEDs 50. The plurality of first LEDs 50 of the first light source 18 are disposed on one of the right casing 22 of the right cup 12 and the left casing 28 of the left cup 14.

The second light source 20 is preferably a plurality of second LEDs 56. The plurality of second LEDs 56 of the second light source 20 are disposed on one of the right casing 22 of the right cup 12 and the left casing 28 of the left cup 14.

The plurality of first LEDs 50 of the first light source 18 and the plurality of second LEDs 56 of the second light source 20 have electromagnetic radiation wavelengths in a range of 1.0 nanometer to 1.0 millimeter, including ultra violet light electromagnetic radiation wavelengths in a range of 1.0 nanometer to 400.0 nanometers, visible light electromagnetic radiation wavelengths in a range of 400.0 nanometers to 700.0 nanometers, and infra red light electromagnetic radiation wavelengths in a range of 700.0 nanometers to 1.0 millimeter, as summarized below.

| LIGHT TYPE | ELECTROMAGNETIC RADIATION WAVELENGTH |
|---|---|
| Ultra Violet Light | 1.0 Nanometer to 400.0 Nanometers |
| Visible Light | 400.0 Nanometers to 700.0 Nanometers |
| Infra Red Light | 700.0 Nanometers to 1.0 Millimeter |

Figure 4:
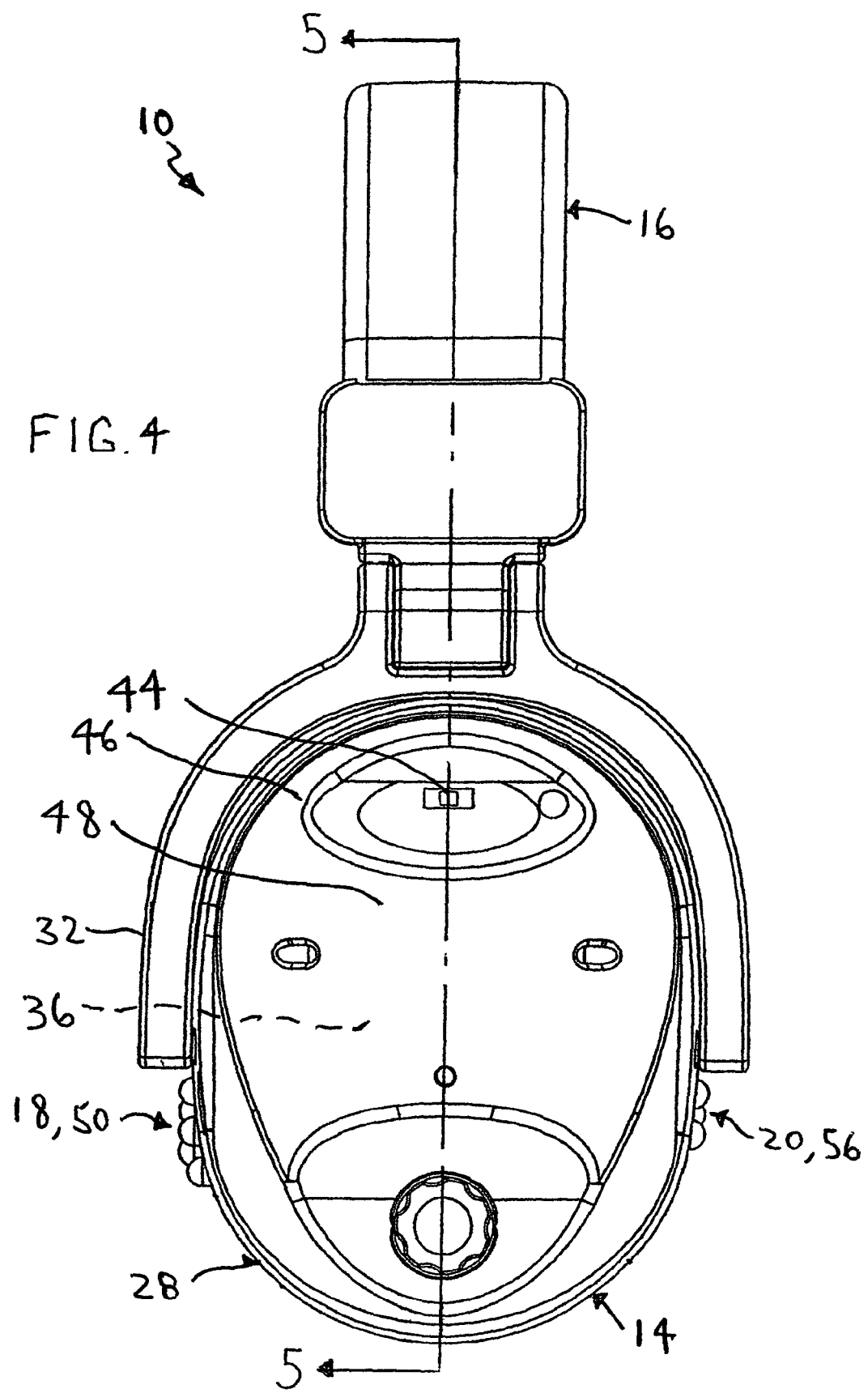
FIG. 4 is a diagrammatic left side elevational view taken generally in the direction of ARROW 4 in FIG. 1 of the combination hearing protector and illumination provider of the embodiments of the present invention.
Figure 5:
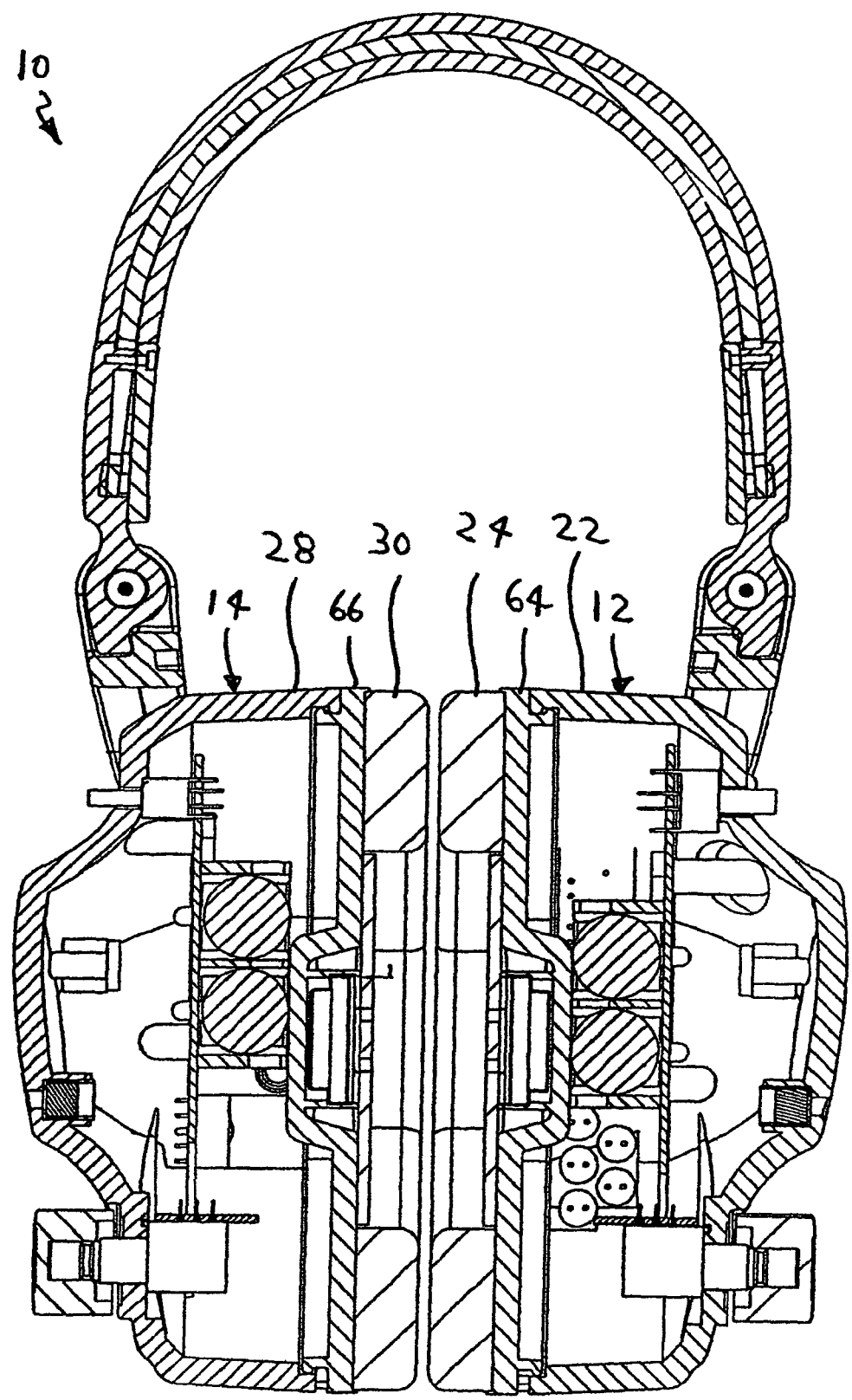
FIG. 5 is a diagrammatic cross sectional view taken along LINE 5-5 in FIG. 4.

As further shown in FIG. 5, which is a diagrammatic cross sectional view taken along LINE 5-5 in FIG. 4, the right cup 12 further comprises a right sound barrier 64. The right sound barrier 64 of the right cup 12 is disposed across the right casing 22 of the right cup 12, where the right pad 24 of the right cup 12 meets the right casing 22 of the right cup 12 so as to be sandwiched therebetween.

The left cup 14 further comprises a left sound barrier 66. The left sound barrier 66 of the left right cup 14 is disposed across the left casing 28 of the left cup 14, where the left pad 30 of the left cup 14 meets the left casing 28 of the left cup 14 so as to be sandwiched therebetween.

C. Conclusions

It will be understood that each of the elements described above or two or more together may also find a useful application in other types of constructions differing from the types described above.

While the embodiments of the present invention have been illustrated and described as embodied in a combination hearing protector and illumination provider, however, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

Without further analysis the foregoing will so fully reveal the gist of the embodiments of the present invention that others can by applying current knowledge readily adapt them for various applications without omitting features that from the standpoint of prior art fairly constitute characteristics of the generic or specific aspects of the embodiments of the present invention.

The invention claimed is:

1. A combination hearing protector and illumination provider, comprising:
   a) a right cup;
   b) a left cup;
   c) a band;
   d) a first light source; and
   e) a second light source;
   wherein said right cup is for covering the right ear of a user;
   wherein said left cup is for covering the left ear of the user;
   wherein said band connects said right cup to said left cup;
   wherein said band is for wearing over the top of the head of the user;
   wherein said first light source is operatively connected to one of said right cup and said left cup;
   wherein said first light source is for facing in a direction that is one of forward of the user and rearward of the user;
   wherein said second light source is operatively connected to one of said right cup and said left cup;
   wherein said second light source is for facing in a direction that is the other of forward of the user and rearward of the user; and
   wherein said first light source and said second light source simultaneously illuminate in opposite directions to each other for illuminating forward of the user and rearward of the user.

2. The combination of claim 1, wherein said right cup comprises a right casing; and
   wherein said right casing of said right cup is operatively connected to one end of said band.

3. The combination of claim 2, wherein said right cup comprises a right pad;
   wherein said right pad of said right cup is for providing comfort for the right ear of the user; and
   wherein said right pad of said right cup is detachably mounted to said right casing of said right cup so as to allow replacement of said right pad of said right cup and servicing access into said right casing of said right cup when necessary.

4. The combination of claim 2, wherein said left cup comprises a left casing; and
   wherein said left casing of said left cup is operatively connected to the other end of said band.

5. The combination of claim 4, wherein said left cup comprises a left pad;
   wherein said left pad of said left cup is for providing comfort for the left ear of the user; and
   wherein said left pad of said left cup is detachably mounted to said left casing of said left cup so as to allow replacement of said left pad of said left cup and servicing access into said left casing of said left cup when necessary.

6. The combination of claim 4, wherein said right cup comprises a right power supply interface;
   wherein said right power supply interface of said right cup is disposed in said right casing of said right cup;
   wherein said right power supply interface of said right cup is in electrical communication with said first light source; and
   wherein said right power supply interface of said right cup is for electrically communicating with a power supply for powering said first light source.

7. The combination of claim 6, wherein said left cup comprises a left power supply interface;
   wherein said left power supply interface of said left cup is disposed in said left casing of said left cup;
   wherein said left power supply interface of said left cup is in electrical communication with said second light source; and
   wherein said left power supply interface of said left cup is for electrically communicating with a power supply for powering said second light source.

8. The combination of claim 7, wherein said right power supply interface of said right cup and said left power supply interface of said left cup are independent of each other so if said power supply of one of said first light source and said second light source fails, the other of said one of said first light source and said second light source will not fail.

9. The combination of claim 4, wherein said left cup comprises a left activation switch;
   wherein said left activation switch of said left cup is in series electrical communication with both said second light source and said left power supply interface of said left cup to selectively power said second light source;
   wherein said left activation switch of said left cup is disposed in said left casing of said left cup; and
   wherein said left activation switch of said left cup is accessible from an upper portion of an outboard side of said left casing of said left cup.

10. The combination of claim 9, wherein said left activation switch of said left cup is a slide switch.

11. The combination of claim 4, wherein said first light source is a plurality of first LEDs.

12. The combination of claim 11, wherein said plurality of first LEDs of said first light source are disposed on said right casing of said right cup; and
    wherein said plurality of first LEDs of said first light source are visible from one of a front and a rear of said right casing of said right cup, at a lower portion thereof for reducing chances of a light beam from said first light source being reflected back into the eyes of the user wearing eyeglasses.

13. The combination of claim 12, wherein said plurality of first LEDs of said first light source have an electromagnetic radiation wavelength in a range of 1.0 nanometer to 1.0 millimeter.

14. The combination of claim 13, wherein said plurality of first LEDs of said first light source have an ultra violet light electromagnetic radiation wavelength in a range of 1.0 nanometer to 400.0 nanometers.

15. The combination of claim 13, wherein said plurality of first LEDs of said first light source have a visible light electromagnetic radiation wavelength in a range of 400.0 nanometers to 700.0 nanometers.

16. The combination of claim 13, wherein said plurality of first LEDs of said first light source have an infra red light electromagnetic radiation wavelength in a range of 700.0 nanometers to 1.0 millimeter.

17. The combination of claim 12, wherein said second light source is a plurality of second LEDs.

18. The combination of claim 17, wherein said plurality of second LEDs of said second light source are disposed on said left casing of said left cup; and
wherein said plurality of second LEDs of said second light source are visible from the other of a front and a rear of said left casing of said left cup, at a lower portion thereof for reducing chances of a light beam from said second light source being reflected back into the eyes of the user wearing eyeglasses.

19. The combination of claim 18, wherein said plurality of second LEDs of said second light source have an electromagnetic radiation wavelength in a range of 1.0 nanometer to 1.0 millimeter.

20. The combination of claim 19, wherein said plurality of second LEDs of said second light source have an ultra violet light electromagnetic radiation wavelength in a range of 1.0 nanometer to 400.0 nanometers.

21. The combination of claim 19, wherein said plurality of second LEDs of said second light source have a visible light electromagnetic radiation wavelength in a range of 400.0 nanometers to 700.0 nanometers.

22. The combination of claim 19, wherein said plurality of second LEDs of said second light source have an infra red light electromagnetic radiation wavelength in a range of 700.0 nanometers to 1.0 millimeter.

23. The combination of claim 17 wherein said plurality of second LEDs of said second light source are one of in series and in parallel with each other.

24. The combination of claim 11, wherein said plurality of first LEDs of said first light source are one of in series and in parallel with each other.

25. The combination of claim 4, wherein said left cup comprises a left sound barrier; and
wherein said left sound barrier of left cup is disposed across said left casing of said left cup, where said left pad of said left cup meets said left casing of said left cup so as to be sandwiched therebetween.

26. The combination of claim 2, wherein said right cup comprises a right activation switch;
wherein said right activation switch of said right cup is in series electrical communication with both said first light source and said right power supply interface of said right cup to selectively power said first light source;
wherein said right activation switch of said right cup is disposed in said right casing of said right cup; and
wherein said right activation switch of said right cup is accessible from an upper portion of an outboard side of said right casing of said right cup.

27. The combination of claim 26, wherein said right activation switch of said right cup is a slide switch.

28. The combination of claim 2, wherein said right cup comprises a right sound barrier; and
wherein said right sound barrier of said right cup is disposed across said right casing of said right cup, where said right pad of said right cup meets said right casing of said right cup so as to be sandwiched therebetween.

29. The combination of claim 1, wherein said band is made from a material selected from the group consisting of metal, plastic, and combinations thereof.

* * * * *